United States Patent [19]

Takei et al.

[11] Patent Number: 4,868,163

[45] Date of Patent: Sep. 19, 1989

[54] TRANSPARENT OR SEMITRANSPARENT JELLY-LIKE COSMETIC COMPOSITION

[75] Inventors: Hiroko Takei, Tokyo; Toshiyuki Suzuki, Ichikawa; Tsuyoshi Otomo, Funabashi; Ichiro Tokimitsu, Tokyo, all of Japan

[73] Assignee: Kao Corporation, Tokyo, Japan

[21] Appl. No.: 102,737

[22] Filed: Sep. 30, 1987

[30] Foreign Application Priority Data

Oct. 2, 1986 [JP] Japan ................. 61-235232

[51] Int. Cl.$^4$ ............... A61K 7/48; A61K 7/50; A61K 9/10
[52] U.S. Cl. ................... 514/76; 514/77; 514/143; 514/784; 514/785; 514/788
[58] Field of Search ............ 514/76, 77, 143, 784, 514/785, 788

[56] References Cited

U.S. PATENT DOCUMENTS 4,670,575 6/1987 Kurosaki et al. ............... 558/146
4,704,220 11/1987 Goddard et al. ............... 252/75

FOREIGN PATENT DOCUMENTS 227012 1/1987 European Pat. Off. .
0227012 7/1987 European Pat. Off. .
2139112 11/1984 United Kingdom .

OTHER PUBLICATIONS

Sagarin, *Cosmetics Science & Technology*, pp. 81–97 (1957)
Imokawa, Chem. Abst. 95:117415s (1981).
Deguchi et al., Chem. Abst. 96:70797w (1982).
Imokawa, Chem. Abst. 90:56731q (1979).
Yamasaki et al., Chem. Abst. 107:204943x (1987).
Chem. Abstracts 102:12205h (1985).
Patent Abstracts of Japan, vol. 10, No. 262 (C-371)[2318] Sep. 6, 1986, JP 61-86940.

*Primary Examiner*—Dale R. Ore
*Attorney, Agent, or Firm*—Oblon, Spivak, McClelland, Maier & Neustadt

[57] ABSTRACT

A transparent or semitransparent jelly-like cosmetic composition comprises a monoalkyl phosphate having a β-branched alkyl group, water, an oil which is liquid at room temperature, and an alcohol.

The cosmetic composition is highly safe and has good moisturizing effect. Therefore, it can be used as a base for a massage cream, a body treatment, a hand cream, a hair conditioner and the like.

2 Claims, No Drawings

TRANSPARENT OR SEMITRANSPARENT JELLY-LIKE COSMETIC COMPOSITION

BACKGROUND OF THE INVENTION

1. Field of the Invention

The present invention relates to a transparent or semitransparent jelly-like cosmetic composition, and more particularly to a transparent or semitransparent jelly-like cosmetic composition comprising a monoalkyl phosphate having a β-branched alkyl group, being highly safe and having good moisturizing effect, that is, an association structure is formed on the skin surface and the hair, so that moisture and oil are remained even after the cosmetic composition is washed away with water.

2. Description of the Prior Art

Heretofore, as a method of preparing a transparent or semitransparent jelly-like cosmetic composition, have been known, for example, (1) a method wherein an oil is added into a system of a nonionic surface active agent/water/polyol (Japanese patent application Laid-Open No. 37709/1986), (2) a method wherein a water-soluble polymer such as a carboxyvinyl polymer is employed, and (3) a method wherein an oil is gelled with a fatty acid soap, dextrin fatty acid ester, or the like. As a conventional method of allowing a surface active agent to remain on the skin or hair, is known (4) a method wherein a cationic surface active agent is incorporated into a cosmetic composition as in the case of a rinsing agent.

However, because the stability of the system in the method (1) is liable to be affected by temperature, the method has some disadvantages, such as the temperature stability is poor and the type of oil to be incorporated is restricted. Since, in the method (2), an oil cannot be added, the affinity of the prepared cosmetic composition to the skin and so on is not good, and when the cosmetic composition is washed with water, nothing remains on the skin and so on. The cosmetic composition prepared by the method (3) makes one's skin feel a glow because of fatty acid ester oils involved therein. Further, since the composition is highly hydrophilic and can be easily washed away with water, only the oil remains disadvantageously on the skin or hair. In the case of the method (4), there is a little doubt about the safety of cationic surface active agents to be incorporated, and the feeling of after use of the cosmetic composition is not good due to the sliminess of the cationic surface active agent involved therein.

Therefore, it has been desired to develop a transparent or semitransparent jelly-like cosmetic composition that is free from the above disadvantages and has a high moisturizing effect.

SUMMARY OF THE INVENTION

The present inventors made intensive studies in order to obtain a transparent or semitransparent jelly-like cosmetic composition. As a result, it was found that a transparent or semitransparent jelly-like cosmetic composition which is strong against water and has a high moisturizing effect can be obtained by employing as an active agent a monoalkyl phosphate having a specific branched chain and incorporating water, an alcohol and an oil. The present invention was accomplished based on the above finding.

Accordingly, an object of the present invention is to provide a transparent or semitransparent jelly-like cosmetic composition comprising the following components (a) to (d):

(a) a monoalkyl phosphate represented by the general formula (I):

wherein R represents a β-branched alkyl group having 8 to 36 carbon atoms, X represents an alkali metal, a basic amino acid or an organic base;

(b) water;

(c) an oil that is liquid at room temperature; and (d) an alcohol.

DETAILED DESCRIPTION OF THE INVENTION AND PREFERRED EMBODIMENTS

In the present invention, the monoalkyl phosphates (I) used as the component (a) are those having a branch at the β-position of the alkyl group, and such monoalkyl phosphates (I) can be prepared, for example, by processes disclosed in Japanese patent application Laid-Open Nos. 180496/1983 and 17594/1986. Of these monoalkyl phosphates (I), preferable ones include those wherein R is a β-branched alkyl group represented by the following formula (II):

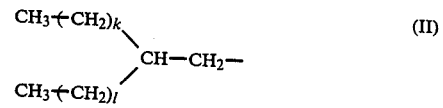

wherein k is a number of 2 to 18, and l is a number of 2 to 14, provided that k+l is 4 to 32, preferably 10 to 18, and the counter ion X is an alkali metal such as lithium, potassium and sodium, a basic amino acid such as arginine, ornithine, lysine, oxylysine, and an alkanolamine containing a hydroxylalkyl group having 2 to 3 carbon atoms such as triethanolamine and monoethanolamine.

As an oil, the component (C), which is liquid at room temperature, any of hydrocarbons, higher alcohols, higher fatty acids, higher fatty acid esters, animals and vegetable fats and oils, cholesterol esters of fatty acids, glycerine esters of higher fatty acids, rosin derivatives, silicone oils and the like which are liquid at room temperature can be used. Of these, isostearyl cholesteryl ester; di- or triglyceride of 2-ethylhexanoic acid, myristic acid, oleic acid, isostearic acid or the like; octyldodecyl myristate; squalane; di-2-ethylhexanoic acid neopentylglycol ester; dimethyl polysiloxane; isopropyl myristate and the like are preferred. These oils may be used alone or in combination.

As an alcohol of the component (d) can be mentioned monoalcohols such as ethanol as well as polyols such as glycerine, ethylene glycol, diethylene glycol, triethylene glycol, hexanediols, butylene glycol, heptanediols, propylene glycol, sorbitol and maltitol. Of these, ethanol, glycerine, propylene glycol, sorbitol and the like are preferred.

The present transparent or semitransparent jelly-like cosmetic composition can be prepared in a usual manner, and preferably can be prepared by mixing and stirring uniformly the components (a), (b) and (d), and then adding the component (c) thereto. This preparation can be carried out at room temperature, except some cases where, for example, the starting materials cannot be dissolved at room temperature.

In the present invention, the proportions of the components of the jelly-like cosmetic composition are such that the component (a) is in the range of 0.05 to 5 wt %, particularly in the range of 0.5 to 2 wt %, the component (b) is in the range of 0.5 to 50 wt %, particularly in the range of 2 to 30 wt %, the component (c) is in the range of 25 to 95 wt %, and the component (d) is in the range of 2 to 50 wt %, particularly in the range of 8 to 40 wt %.

In the jelly-like cosmetic composition of the present invention, to provide the composition with self-emulsifiability required when it is washed away with water, and to make one's feeling better after the composition is washed away, a nonionic surface active agent of sorbitan fatty acid type, polyoxyethylene alkyl ether type or the like can be added. However, an excess amount of nonionic surface active agent makes the cosmetic composition to be turbid, and therefore it is preferable that the amount of such a nonionic surface active agent to be added is up to 3%.

The jelly-like cosmetic composition of the present invention can include any known ingredients to be incorporated into a cosmetic composition, such as humectants, solid oils, waxes, blood circulation facilitators, coolants, UV absorbents, perspiration depressing agents, germicides, skin cell activators, antioxidants, perfumes, colorants and the like.

The monoalkyl phosphate (I) according to the invention has a property to form such a structure as a lamellar liquid crystal structure and a liposome (vesicle) structure together with water and an alcohol, even if the concentration of the monoalkyl phosphate (I) is low. Therefore, it is considered that an oil is kept stably in the structure to provide a transparent or semitransparent jelly-like cosmetic composition. When the cosmetic composition of the present invention is used, the above structure is formed on the skin, so that when the composition on the skin is washed away with water, the structure keeps water and oil on the skin to exhibit the moisturizing effect.

The transparent or semitransparent jelly-like cosmetic composition of the invention is good in temperature stability, and various types of oils can be incorporated thereinto. Even after the cosmetic composition is applied to the skin and then washed away with water, the above structure which is quite safe remains on the skin, so that the skin is provided with an excellent mositurized feel.

Therefore, the jelly-like cosmetic composition of the present invention can be used as a base for a massage cream, a body treatment, a cleansing agent, a sun screen, a hand cream, a base cream for a foundation, a moisturizing cream, a hair treatment, a hair conditioner, etc.

The invention will now be explained with reference to the following Examples.

EXAMPLE 1

Each transparent jelly-like cosmetic composition having a formulation shown below was prepared, and was applied to one's skin (arm). After washing out the composition with water, it was determined whether there was water repellency on the skin or not and whether there remained the moisturizing component or not. The results are shown below.

| (Formulation) | Inventive Composition (%) | Comparative Composition A (%) | Comparative Composition B (%) |
| --- | --- | --- | --- |
| (1) 2-Octalauryl phosphate arginine salt | 0.5 | — | — |
| (2) Lauryl phosphate arginine salt | — | 0.5 | — |
| (3) Sodium oleate | — | — | 0.8 |
| (4) Glycerine | 5 | 5 | 3 |
| (5) Water | 1 | 1 | 2 |
| (6) 2-Ethylhexanoic acid diglyceride | 93.5 | 93.5 | 94.2 |

(Preparation)

Ingredient (1) or (2) and ingredients (4) and (5) were dissolved and mixed (by heating if required). To the thus obtained mixture, the oil was slowly added under agitation.

TABLE 1

| (Results) | Inventive Composition | Comparative Composition A | Comparative Composition B |
| --- | --- | --- | --- |
| Water repellency | noted | unnoted | unnoted |
| Moisturizing component* | noted | a very small amount was detected | unnoted |

*The applied part was extracted with an organic solvent and the extract was analyzed by HPLC.

EXAMPLE 2

Each massage cream having a formulation shown in Table 2 was prepared in the same manner as Example 1. The state of the massage cream and the temperature stability after one month preservation were observed.

TABLE 2

| (Formulation) | Inventive Composition | | | Comparative Composition | | |
| --- | --- | --- | --- | --- | --- | --- |
| | A | B | C | D (%) | E | F |
| 2-Octalauryl phosphate arginine salt | 0.5 | 0.5 | 0.5 | — | — | — |
| Water | 1.6 | 1.6 | 1.6 | 4 | 4 | 4 |
| Glycerine | 8 | 8 | 8 | 1.5 | 1.5 | 1.5 |
| 1,3-Butylene glycol | 2 | 2 | 2 | 6 | 6 | 6 |
| Polyoxyethylene sorbitan monostearate | — | — | — | 5 | 5 | 5 |
| 2-Ethylhexanoic acid diglyceride | 87.9 | — | — | 83.5 | — | — |
| 2-Ethylhexanoic acid triglyceride | — | 87.9 | — | — | 83.5 | — |
| Liquid paraffin | — | — | 87.9 | — | — | 83.5 |

TABLE 3

| | (Results) | | | | | |
| --- | --- | --- | --- | --- | --- | --- |
| | | Temperature stability* (after one month preservation) | | | | |
| | State | −5° C. | 10° C. | 25° C. | 40° C. | 50° C. |
| A | transparent gel | O | O | O | O | O |
| B | transparent gel | O | O | O | O | O |
| C | transparent gel | O | O | O | O | O |
| D | transparent gel | Δ | X | X | X | X |

TABLE 3-continued

| | (Results) | | | | |
|---|---|---|---|---|---|
| | Temperature stability* (after one month preservation) | | | | |
| State | −5° C. | 10° C. | 25° C. | 40° C. | 50° C. |
| E transparent gel | O | Δ | X | X | X |
| F opaque gel | Δ | X | X | X | X |

*The evaluation was made according to the following criteria:
O: No change was observed in the state.
Δ: Lowering of the viscosity and separation of oil were slightly observed.
X: The viscosity lowered conspicuously and the oil separated.

EXAMPLE 3

Body Treatment

A body treatment having a formulation shown below was prepared. The feeling of use and the feeling of after-use of the body treatment were evaluated by 10 female monitors, and compared with those of Commercial Product A which is an aqueous transparent gel-like body treatment containing as a humectant propylene glycol, an extract of seaweeds and the like, and as a thickener carboxyvinyl polymer, and Commerical Product B which is W/O type mikly emulsion body treatment containing oily ingredients such as cetanol, olive oil and the like. The results are shown in Table 4.

| | (Formulation) | |
|---|---|---|
| (1) | 2-Hexadecyl phosphate arginine salt | 0.3 (%) |
| (2) | Water | 1.4 |
| (3) | Glycerine | 3.89 |
| (4) | Oils* | 44.5 |
| (5) | Carboxyvinyl polymer | 0.1 |
| (6) | 10% aqueous sodium hydroxide solution | 0.4 |
| (7) | Glycerine | 35 |
| (8) | Ethanol | balance |

*Oils: Inventive Product A
  squalane 24.5%
  jojoba oil 12%
  vaseline 8%
Inventive Product B
  2-ethylhexanoic acid diglyceride 30.0%
  isostearic acid cholesteryl ester 10.0%
  octyldodecyl myristate 4.5%

(Preparation)

Ingredients (1), (2) and (3) were stirred at 60° C. to obtain a uniform mixture, and then ingredient (4) was added. To the mixture were added a previously prepared mixture of ingredients (5) through (8) to obtain a transparent gel-like body treatment.

TABLE 4

| | (Results) | | | |
|---|---|---|---|---|
| | Inventive Product | | Commercially available body treatment | |
| | A | B | A | B |
| Item of Evaluation** | | | | |
| Affinity to the skin | 4 | 5 | 4 | 3 |
| Transparency | 5 | 4 | 3 | 1 |
| Washability with water | 3 | 3 | 5 | 2 |
| Feeling of after-use | 5 | 5 | 2 | 5 |
| Moistened feel | 4 | 5 | 3 | 3 |
| Feeling of use | 3 | 4 | 4 | 2 |

**The evaluation was graded into five rates. The higher rate shows the better evaluation.

EXAMPLE 4

Transparent Jelly-like Cleansing:

A transparent jelly-like cleansing having a formulation shown below was prepared, and was compared with a transparent gel-like cleansing (soluble in water) and a cleansing cream. The results are shown in Table 5.

| (Formulation) | |
|---|---|
| Cleansing of the present invention: | |
| 2-Hexadecyl phosphate arginine salt | 1.0 (%) |
| Water | balance |
| Glycerine | 25 |
| Sorbitol | 10 |
| Di-2-ethylhexanoic acid neopentyl glycol | 60 |
| Hardened castor oil | 2.5 |
| Comparative Cleansing G (Transparent Gel-like Cleansing, Soluble in Water): | |
| Carboxyvinyl polymer | 0.3 (%) |
| 10% sodium hydroxide | 1.2 |
| 1,3-Butylene glycol | 10 |
| Polyoxyethylene methylglycoside | 8 |
| Water | balance |
| Comparative Cleansing H (Cleansing Cream): | |
| Polyoxyethylene sorbitan monostearate (EO = 20) | 3 (%) |
| Sorbitan monostearate | 2 |
| Liquid paraffin | 30 |
| Squalane | 20 |
| 1,3-Butylene glycol | 5 |
| Water | balance |

TABLE 5

| | (Results) | | |
|---|---|---|---|
| | Inventive Product | Comparative Product | |
| | | G | H |
| Item of Evaluation* | | | |
| Cleansing effect | 5 | 2 | 4 |
| Washability with water | 4 | 5 | 2 |
| Refreshing feel after washing | 3 | 3 | 2 |
| Moistened feel after washing | 4 | 2 | 2 |
| Sliminess after washing | 4 | 5 | 2 |

*The evaluation was carried out in the same way as in Example 3. With respect to the sliminess, the higher the rate, the lower the sliminess.

EXAMPLE 5

| Sun Screen Jelly: (Formulation) | |
|---|---|
| 2-Octalauryl phosphate arginine salt | 0.9 (%) |
| Water | 1.6 |
| Glycerine | 6.0 |
| 1,3-Butylene glycol | 3.5 |
| Ethanol | 12.5 |
| Dimethylpolysiloxane | 28.0 |
| Olive oil | 42.0 |
| 2-Ethylhexylparadimethyl aminobenzoate | 4.0 |
| Perfume | suitable amount |
| Preservative | suitable amount |

EXAMPLE 6

| Jelly-like Hand Cream: (Formulation) | |
|---|---|
| 2-Hexadecyl phosphate arginine salt | 1.2 (%) |
| Water | 3.6 |
| Glycerine | 12.0 |
| Dipropylene glycol | 8.0 |
| Isopropyl myristate | 36.0 |
| Liquid paraffin | 35.5 |
| Cetanol | 0.4 |
| Stearyl alcohol | 0.6 |
| Perfume | suitable amount |
| Preservative | suitable amount |

EXAMPLE 7

| Jelly-like Hand Cream: (Formulation) | |
|---|---|
| 2-Hexadecyl phosphate arginine salt | 1.2 (%) |
| Water | 3.6 |
| Glycerine | 12.0 |
| Dipropylene glycol | 8.0 |
| Isostearyl diglyceride | 36.0 |
| Liquid paraffin | 35.5 |
| Cetanol | 0.4 |
| Stearyl alcohol | 0.6 |
| Perfume | suitable amount |
| Preservative | suitable amount |

WHAT IS CLAIMED IS:

1. A transparent or semitransparent jelly-like cosmetic composition consisting essentially of the following components (a) to (d):
   (a) 0.05–5 wt. % of a monoalkyl phosphate represented by the general formula (I):

$$R-O-\overset{\overset{O}{\|}}{\underset{OH}{P}}-OX \quad (I)$$

wherein R represents a β-branched alkyl group having 8 to 36 carbon atoms, X represents an alkali metal, a basic amino acid or an organic base;
   (b) 0.05–50 wt. % of water;
   (c) 25–95 wt. % of an oil that is liquid at room temperature; and
   (d) 2–50 wt. % of an alcohol.

2. A transparent or semitransparent jelly-like cosmetic composition according to claim 1, a group R in said monoalkyl phosphate (I) of the component (a) being a β-branched alkyl group represented by the following formula (II):

$$\begin{array}{c} CH_3\text{-}(CH_2)_k \\ \phantom{CH_3\text{-}(CH_2)}\diagdown \\ \phantom{CH_3\text{-}(CH_2)_k}CH\text{-}CH_2\text{-} \\ \phantom{CH_3\text{-}(CH_2)}\diagup \\ CH_3\text{-}(CH_2)_l \end{array} \quad (II)$$

wherein k is a number of 2 to 18, and l is a number of 2 to 14.

* * * * *